United States Patent
Osborne et al.

(10) Patent No.: US 9,920,355 B2
(45) Date of Patent: Mar. 20, 2018

(54) METHOD FOR FRAGMENTING AND LIGATING ADAPTORS ONTO A NUCLEIC ACID, AND KIT FOR PERFORMING THE SAME

(71) Applicant: Population Genetics Technologies Ltd., Cambridge (GB)

(72) Inventors: Robert Osborne, Great Chesterford (GB); Samuel Woodhouse, Cambridge (GB); Esther Musgrave-Brown, Cambridge (GB)

(73) Assignee: POPULATION GENETICS TECHNOLOGIES LTD., Cambridge (GB)

( * ) Notice: Subject to any disclaimer, the term of this patent is extended or adjusted under 35 U.S.C. 154(b) by 0 days.

(21) Appl. No.: 15/526,740

(22) PCT Filed: Nov. 12, 2015

(86) PCT No.: PCT/IB2015/058762
§ 371 (c)(1),
(2) Date: May 12, 2017

(87) PCT Pub. No.: WO2016/083933
PCT Pub. Date: Jun. 2, 2016

(65) Prior Publication Data
US 2017/0335371 A1    Nov. 23, 2017

(30) Foreign Application Priority Data
Nov. 26, 2014 (GB) .................................. 1421003.3

(51) Int. Cl.
*C12P 19/34* (2006.01)
*C12Q 1/68* (2018.01)

(52) U.S. Cl.
CPC ......... *C12Q 1/6806* (2013.01); *C12Q 1/6869* (2013.01)

(58) Field of Classification Search
USPC .............................................. 435/6.12, 91.2
See application file for complete search history.

(56) References Cited

U.S. PATENT DOCUMENTS

| 8,653,007 B2 | 2/2014 | Zheng et al. |
| 9,422,594 B2 | 8/2016 | McKernan |
| 2011/0033854 A1 | 2/2011 | Drmanac et al. |
| 2014/0178873 A1* | 6/2014 | Brachmann .......... C12Q 1/6858 435/6.11 |

FOREIGN PATENT DOCUMENTS

WO    WO 2004/081183    9/2004

OTHER PUBLICATIONS

Chen, et al., "The Master (methylation-assisted tailorable ends rational) ligation method for seamless DNA assembly", Nucleic Acids Research, 2013, 41(8): e93.
Davey, et al., "Genome-wide genetic marker discovery and genotyping using next-generation sequencing", Nature Reviews Genetics, 2011, 12(7): 499-510.
Huang, et al., "High-throughput sequencing of methylated cytosine enriched by modification-dependent restriction endonuclease MspJI", BMC Genetics, BioMed Central, 2013, 14(1):56.
Wetzel, et al., "A RT/PCR-partial restriction enzymatic mapping (PREM) method for the molecular characterisation of the large satellite RNAs of Arabis mosaic virus isolates", Journal of Virological Methods, 2006, 132: 97-103.

* cited by examiner

*Primary Examiner* — Kenneth R Horlick
(74) *Attorney, Agent, or Firm* — James S. Keddie; Bozicevic, Field & Francis, LLP (57) ABSTRACT

Providing herein, among other things, is a method for preparing a nucleic acid for sequencing. In some embodiments, the method comprises a) amplifying a nucleic acid template using a dNTP mix that contains 5-methyl dCTP, thereby producing product nucleic acid molecules that contains methylcytosines; b) digesting the product nucleic acid molecules with a methylation-dependent restriction endonuclease, thereby cleaving the product nucleic acid molecules at sites that are adjacent to at least some of the methylcytosine and producing fragments of the product nucleic acid molecules; and c) ligating double-stranded adaptors onto the ends of the fragments to produce adaptor-ligated products.

27 Claims, 5 Drawing Sheets

SEQUENCE LISTING

<160> NUMBER OF SEQ ID NOS: 11

<210> SEQ ID NO 1
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 1
ctgtctctta tacacatct                                                19

<210> SEQ ID NO 2
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 2
gacagagaat atgtgtaga                                                19

<210> SEQ ID NO 3
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 3
agatgtgtat aagagacag                                                19

<210> SEQ ID NO 4
<211> LENGTH: 38
<212> TYPE: DNA
<213> ORGANISM: artificial sequence
<220> FEATURE:
<223> OTHER INFORMATION: synthetic amplification product

<400> SEQUENCE: 4
agatgtgtat aagagacagc tgtctcttat acacatct                           38

<210> SEQ ID NO 5
<211> LENGTH: 38
<212> TYPE: DNA
<213> ORGANISM: artificial sequence
<220> FEATURE:
<223> OTHER INFORMATION: synthetic product

<400> SEQUENCE: 5
tctacacata ttctctgtcg acagagaata tgtgtaga                           38

<210> SEQ ID NO 6
<211> LENGTH: 62
<212> TYPE: DNA
<213> ORGANISM: artificial sequence

```
<220> FEATURE:
<223> OTHER INFORMATION: synthetic oligonucleotide

<400> SEQUENCE: 6
aatgatacgg cgaccaccga gatctacact cgtcggcagc gtcagatgtg tataagagac      60
ag                                                                    62

<210> SEQ ID NO 7
<211> LENGTH: 58
<212> TYPE: DNA
<213> ORGANISM: Artificial sequence
<220> FEATURE:
<223> OTHER INFORMATION: synthetic oligonucleotide

<400> SEQUENCE: 7
caagcagaag acggcatacg agatgtctcg tgggctcgga gatgtgtata agagacag        58

<210> SEQ ID NO 8
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 8
ctgtctctta tacacatct                                                  19

<210> SEQ ID NO 9
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 9
gacagagaat atgtgtaga                                                  19

<210> SEQ ID NO 10
<211> LENGTH: 62
<212> TYPE: DNA
<213> ORGANISM: artificial sequence
<220> FEATURE:
<223> OTHER INFORMATION: synthetic oligonucleotide
<220> FEATURE:
<221> NAME/KEY: sample indexer
<222> LOCATION: (30)..(37)
<223> OTHER INFORMATION: Ns are a sample identifier sequence

<400> SEQUENCE: 10
aatgatacgg cgaccaccga gatctacact cgtcggcagc gtcagatgtg tataagagac      60
ag                                                                    62

<210> SEQ ID NO 11
<211> LENGTH: 58
<212> TYPE: DNA
<213> ORGANISM: artificial sequence
<220> FEATURE:
<223> OTHER INFORMATION: synthetic oligonucleotide

<400> SEQUENCE: 11
caagcagaag acggcatacg agatgtctcg tgggctcgga gatgtgtata agagacag        58
```

METHOD FOR FRAGMENTING AND LIGATING ADAPTORS ONTO A NUCLEIC ACID, AND KIT FOR PERFORMING THE SAME

CROSS-REFERENCING

This application claims the benefit of United Kingdom Patent Application Serial No. 1421003.3, which application is incorporated by reference herein.

BACKGROUND

A typical sequencing workflow proceeds via the following steps: a) fragmenting the target DNA to make fragments; b) ligating adaptors to the fragments; c) amplifying the adaptor-ligated fragments, and d) sequencing the amplification products. In some methods, the fragmenting and ligating steps are mediated by a transposase (see, e.g., Caruccio, Methods Mol Biol. 2011; 733:241-55). In other methods, the fragmenting is done mechanically (e.g., by sonication or shearing) or using a double stranded DNA "dsDNA" fragmentase enzyme. In these methods (e.g., the mechanical or fragmentase methods), after the DNA is fragmented, the ends are polished and ligated to the adaptor.

Methods that rely on mechanical fragmentation and enzymes that generate dsDNA breaks (e.g. NEBNext dsDNA Fragmentase, New England Biolabs) require additional steps to prepare the fragments for ligation. For example, in both cases the ends of the fragments need to be polished using a polymerase, and in some cases, the polished fragments need to be treatment with a kinase to ensure that all of the 5' ends are phosphorylated. In addition, in many protocols the fragments are dA-tailed before ligation. These additional steps add significant technical complexity to the protocol.

Current fragmentation methods that rely on an enzyme (e.g., transposase or dsDNA fragmentase) are also limited because they are highly sensitive to the ratio of enzyme to DNA in the reaction. If too much DNA is included then the template is poorly fragmented. If too little DNA is included then the template is overly fragmented. This means that the amount template DNA must be carefully quantified before fragmentation and the reaction time and amount of enzyme should be carefully controlled to obtain a desired level of fragmentation. Finally, enzyme-based reactions are driven by an excess of enzyme and need to be quickly stopped to prevent excess fragmentation. This often involves addition of a stop buffer, which can adversely affect downstream processing steps or require extra cleanup steps. Further, when several samples are being processed, it can be difficult to ensure that fragmentation reaction time is uniform across the samples.

Moreover, transposase-mediated methods also have a bias for certain insertion sites (see, e.g., Green et al Mobile DNA 2012, 3:3) and, as such, the fragmentation is not truly random. Transposase-mediated methods also rely on conserved 'arm' sequences that contain sequence elements that are required for transposon-arm complex formation and the fragmentation/ligation reaction. This makes the adaptor sequences difficult to customize. While it is in theory possible to add molecular barcodes and the like 5' of the arm sequences (outside of the transposase binding sites), this modification adds sequence freight to the resultant sequence reads, effectively shortening the length of the sequence reads.

Peters et al (Nature. 2012 487:190-5) developed a protocol called Controlled Random Enzymatic Fragmentation (CoRE) to randomly fragment DNA. This protocol involves incorporating dUTP into a product using a DNA polymerase, and then treating the product (which contains uracil) with uracil DNA glycosylase (UDG) and an endonuclease (endonuclease IV) to fragment the product. The ratio of dUTP/dTTP controls the average fragment length after endonuclease treatment. However, the Peters protocol requires multiple enzymatic steps, including treatment by: (1) shrimp alkaline phosphatase (SAP), (2) UDG, (3) EndoIV, (4) *E. coli* DNA polymerase I, (5) SAP and (6) ligase. Moreover, the ability of a polymerase to incorporate dUTP varies greatly from polymerase to polymerase and, indeed, there are many polymerases, including proofreading DNA polymerases, that cannot incorporate dUTP. Thus, Peter's method has limited utility.

Drmanac (US2011033854) describes a multi-step method for turning a "long" fragment into a population of smaller, blunt ended, fragments that can be ligated to adaptors, amplified and sequenced. The Drmanac method involves replacing nucleotides with nucleotide analogs, creating "gapped" nucleotides (i.e., nucleic acids that contain nicks or gaps), and nick translating (i.e., copying) the gaps using the other strand as a template, to produce blunt-ended fragments. In some cases, Drmanac performs his method by incorporating dUTP and d$^m$CTP into the "long" fragment using a polymerase, deglycosylating the uridines (using UDG), removing the deglycosylated nucleotides (using an endonuclease), making double stranded breaks near the $^m$CTPs (using McrBC), and then nick translating the digested product using a strand-displacing polymerase to blunt-ended fragments (see FIG. 2 and para. 82). Next, adaptors are ligated and the fragments can be amplified and sequenced. Variations of Drmanac's method include treatments by a kinase and/or an alkaline phosphatase, as well as polishing and A-tailing.

In addition to being difficult to implement because it is a technically complex, multi-step process, Drmanac's method also suffers from a number of acute problems, particularly for many sequencing applications.

For example, the Drmanac the method is complicated by the fact that while the nick translation step can, in theory, be done using a proofreading polymerase (i.e., the type that would be more suitable for sequencing applications because they have a higher fidelity, e.g., Pfu), the use of such a polymerase would lead to degradation of non-protected 3' overhangs. This will result in problems with ligation and, in addition, would lead to products that can self-ligate (e.g., circularize). Drmanac points out that one could alternatively use a non-proofreading polymerase (e.g., Taq). However, as would be apparent, the use of a non-proofreading polymerase can lead to a product that contains lots of errors. Further, with respect to the use of non-proofreading polymerases in his method, Drmanac himself states that the process can be hard to control, and will often generate a mixed population of 3' ends, resulting in a low adaptor-to-insert ligation yield. Drmanac proposes to solve some of these problems using special adaptors, ddNTPs, A-tailing, and/or an alkaline phosphatase treatment, effectively adding even more steps to an already complicated method.

In addition, many, if not most polymerases (including thermostable polymerases with the highest fidelity) either do not incorporate dUTP efficiently or do not recognize templates that contain dUTP, meaning that the initial step of Drmanac's method (i.e., producing a "long" fragment containing uridine and methylcytosine), can only be implemented using a restricted number of polymerase, many of which have a high error rate.

Finally, McrBC is a rather unusual restriction enzyme in that it cuts at an unspecified, variable, position between two methylated cytosines, and the type of ends that it produces are unknown and may vary from site to site. As such, in order to implement Drmanac's method, those sites would have to polished by filling in the 5' overhangs and chewing back the 3' overhangs, which further complicates Drmanac's method and, in addition, would lead to "gaps" in the sequence. Also, McrBC optimally cleaves when the spacing between adjacent methylcytosines cytosines is relatively close together (i.e., from 55 bp to 103 bp). This makes McrBC less than efficient for producing fragments for most sequencing applications (which generally require longer fragments).

The method described herein lacks at least some of the deficiencies listed above and, depending on how the method is implemented, can have other advantages as described below.

SUMMARY

Providing herein, among other things, is a method for preparing a nucleic acid for sequencing. In some embodiments, the method comprises: a) amplifying a nucleic acid template using a dNTP mix that contains 5-methyl dCTP, thereby generating product nucleic acid molecules that contain methylcytosines; b) digesting the product nucleic acid molecules with a methylation-dependent restriction endonuclease, e.g., an MspJI family restriction endonuclease, thereby cleaving the product nucleic acid molecules at sites that are adjacent to at least some of the methylcytosines and producing fragments of the product nucleic acid molecules; and c) directly ligating double-stranded adaptors onto the overhangs of the fragments to produce adaptor-ligated products. In some embodiments the method may additionally comprise: d) amplifying the fragments using primers that hybridize to the adaptors to produce amplification products. Kits are also provided.

Depending on how the method is implemented, the method may have certain advantages over conventional methods. For example:

the length of the fragments produced by the method is solely dependent on the ratio of 5-methyl dCTP to dCTP in the dNTP mix, not the concentration of DNA in the sample or the amount of enzyme used (which is the case for other methods);

the method is not limited by the polymerases that can be used and, as such, the method can be done using virtually any polymerase, including high fidelity thermostable polymerases;

the method is not a complicated, multi-step procedure that uses several incompatible enzymes; in fact, after the initial amplification step, the entire reaction—including adaptor ligation—can be implemented in a single tube without the addition of new reagents;

the method is efficient because digestion by MspJI family restriction endonucleases inherently produces 4 base overhangs, which are very efficient ligation substrates relative to blunt ends;

the method only rarely produces fragments in which the opposite ends are complementary, meaning that those fragments will not simply circularlize during adaptor ligation; and the method can be readily adapted to produce fragments that have lengths that are more suitable for sequencing applications.

These and other advantages may be apparent in view of the following discussion. Firstly, the length of the fragments is determined by the ratio of 5-methyl dCTP to dCTP in the first amplification step. Assuming that the digestion goes to completion, the length of the fragments is not sensitive to the amount of DNA in the reaction, the reaction time, or the amount of enzyme used. As such, once a suitable ratio of 5-methyl dCTP to dCTP has been determined for one sample, the same ratio can be used for other samples, even for other samples that have a different concentration of DNA or DNA of an unknown DNA concentration. If longer or shorter fragments are required (or, alternatively, if the sample is highly A/T-rich or G/C-rich) then the ratio of 5-methyl dCTP to dCTP can simply be adjusted or different restriction enzymes, or combinations of different restriction enzymes, can be used. The considerations of length and A/T or G/C content may be encountered when analyzing particular genomes or genomic regions or when using different sequencing platforms.

Further, because proof-reading polymerases can incorporate 5-methyl dCTP, the first amplification step may be done using a high fidelity enzyme. Use of a high fidelity enzyme for amplification of a template at the beginning of the protocol can be vitally important in some sequencing applications because, without high fidelity amplification, it is often impossible to determine whether a potential sequence variation corresponds to a low frequency mutation in the sample (i.e., a "minority variant") or a so-called "PCR error" (i.e., an error caused by the mis-incorporation of a nucleotide during polymerization). The ability to controllably fragment a DNA product that has been generated by high fidelity amplification is highly desirable.

Additionally, at a practical level, the restriction endonuclease reaction can be terminated by heat inactivation and because no additional enzyme treatment steps are required between fragmentation and ligation, the ligation reaction can be done in the same buffer as the digestion. Further no specialized, expensive, equipment is required to perform the method, and the adaptors can be customized as needed, e.g., so that the sequencing reads go straight into a molecular barcode sequence, thereby reducing sequencing freight and effectively increasing the length of the sequencing reads.

Further, as noted above, the number of fragmentation breakpoints can be controlled by varying the ratio of 5-methyl dCTP and dCTP in the amplification reaction. Therefore, the number of breakpoints (which, in turn determines the average fragment size) can be tuned to be optimal for a particular genome, genomic region, sequencing platform and/or number of different fragmentation breakpoints required for error-correction, as desired. For example, some sequence analysis protocols involve grouping sequence reads based on their fragmentation breakpoints. As noted above, the method can be tuned to provide an optimum number of "ends" per kilobase of target. The availability of more ends allows the sequence reads to be grouped into more groups and that, in turn, make sequencing more accurate.

Other implementations, embodiments and advantages may be apparent from the description that follows below.

BRIEF DESCRIPTION OF THE DRAWINGS

The skilled artisan will understand that the drawings, described below, are for illustration purposes only. The drawings are not intended to limit the scope of the present teachings in any way.

DEFINITIONS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a framework region" includes reference to one or more framework regions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

"Genetic locus," "locus," or "locus of interest" in reference to a genome or target polynucleotide, means a contiguous sub-region or segment of the genome or target polynucleotide. As used herein, genetic locus, locus, or locus of interest may refer to the position of a nucleotide, a gene or a portion of a gene in a genome, including mitochondrial DNA or other non-chromosomal DNA (e.g., bacterial plasmid), or it may refer to any contiguous portion of genomic sequence whether or not it is within, or associated with, a gene. A genetic locus, locus, or locus of interest can be from a single nucleotide to a segment of a few hundred or a few thousand nucleotides in length or more. In general, a locus of interest will have a reference sequence associated with it (see description of "reference sequence" below).

The terms "plurality", "population" and "collection" are used interchangeably to refer to something that contains at least 2 members. In certain cases, a plurality, population or collection may have at least 10, at least 100, at least 1,000, at least 10,000, at least 100,000, at least $10^6$, at least $10^7$, at least $10^8$ or at least $10^9$ or more members.

The term "adaptor" refers a sequence that is added (e.g., by ligation) to a nucleic acid. An adaptor may be from 5 to 100 bases in length, and may provide, e.g., an amplification primer binding site, a sequencing primer binding site, and/or a molecular barcode such as a sample identifier sequence or molecule identifier sequence. An adaptor may be added to the 5' end, the 3' end, or both ends of nucleic acid molecule. Double stranded adaptors contain a double stranded end that is ligated to a nucleic acid. An adaptor can have an overhang or may be blunt. As will be described in greater detail below, a double stranded adaptor can be added to a fragment by ligating only one strand of the adaptor to the fragment. The sequence of the non-ligated strand of the adaptor may be added to the fragment using a polymerase. Y-adaptors and loop adaptors are type of double-stranded adaptors.

The term "sample identifier sequence", "sample index", "multiplex identifier" or "MID" is a sequence of nucleotides that is appended to a target polynucleotide, where the sequence identifies the source of the target polynucleotide (i.e., the sample from which sample the target polynucleotide is derived). In use, each sample is tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences. A sample identifier sequence may be added to the 5' end of a polynucleotide or the 3' end of a polynucleotide. In certain cases some of the sample identifier sequence may be at the 5' end of a polynucleotide and the remainder of the sample identifier sequence may be at the 3' end of the polynucleotide. When a polynucleotide as an sample identifier sequence at both ends, together, the 3' and 5' sample identifier sequences identify the sample. In many examples, the sample identifier sequence is only a subset of the bases which are appended to a target oligonucleotide.

The term "molecule identifier sequence" (which may also be referred to as a "counter sequence", or "VeriTag" in some instances) is a sequence of nucleotides that can be appended to the nucleic acid fragments of a sample such that the appended sequence of nucleotides, alone or in combination with other features of the fragments, e.g., their fragmentation breakpoints, can be used to distinguish between the different fragment molecules in the sample or a portion thereof. The complexity of a population of molecule identifier sequences used in any one implementation may vary depending on a variety of parameters, e.g., the number of fragments in a sample and/or the amount of the sample that is used in a subsequent step. For example, in certain cases, the molecule identifier sequence may be of low complexity (e.g., may be composed of a mixture of 8 to 1024 sequences). In other cases, the molecule identifier sequence may be of high complexity (e.g., may be composed of 1025 to 1M or more sequences). In certain embodiments, a population of molecule identifier sequences may comprise a degenerate base region (DBR) comprising one or more (e.g., at least 2, at least 3, at least 4, at least 5, or 5 to 30 or more)

nucleotides selected from R, Y, S, W, K, M, B, D, H, V, N (as defined by the IUPAC code), or a variant thereof. In some embodiments, a population of molecule identifier sequences may be made by mixing oligonucleotides of a defined sequence together. In these embodiments, the molecule identifier sequence in each of the oligonucleotides may be error correctable. In the methods described herein, the molecule identifier sequence may be used to distinguish between the different fragments in a portion of an initial sample, where the portion has been removed from the initial sample. The molecule identifier sequences may be used in conjunction with other features of the fragments (e.g., the end sequences of the fragments, which define the breakpoints) to distinguish between the fragments. Molecule identifier sequences are described in (Casbon Nuc. Acids Res. 2011, 22 e81) and have been demonstrated to increase the sensitivity of minority variant detection in HIV (Jabara et al 2011), Pap smears (Kinde et al 2013) and RNA-Seq (Shiroguchi et al 2012).

The term "fragmentation breakpoint" is intended to refer to the site at which a nucleic acid is cleaved to produce a fragment. Two fragments that have the same fragmentation breakpoints have the same sequences at their ends (excluding any adaptor sequences that have been added to the fragments).

The term "minority variant" is defined is a variant that is present a frequency of less than 20%, relative to other molecules in the sample. In some cases, a minority variant may be a first allele of a polymorphic target sequence, where, in a sample, the ratio of molecules that contain the first allele of the polymorphic target sequence compared to molecules that contain other alleles of the polymorphic target sequence is 1:10 or less, 1:100 or less, 1:1,000 or less, 1:10,000 or less, 1:100,000 or less or 1:1M or less. Minority variants of drug resistant HIV are described in Gianella et al (J Infect Dis. (2010) 202: 657-666).

The term "sequence freight" is used to refer to the bases in a sequence read that come from adaptors or primers that do not contain useful information (e.g., bases that are not part of the target fragment or a molecular barcode such as a molecule identifier or sample identifier). These bases are non-informative and usually trimmed before analysis, leading to a shorter sequence read.

The term "defined amount" may be measured in moles, weight or volume if a volume contains a known concentration of nucleic acid. The concentration of nucleic acid in a sample can be determined using any suitable method.

The term "amplifying" is intended to refer to both isothermal amplification methods and methods that require thermocycling (e.g., PCR) Amplification requires increasing the relative concentration of one or more sequences in a sample at least 10-fold, relative to unamplified components of the sample.

The term "nucleic acid template" is intended to refer to the initial nucleic acid molecule that is copied during amplification.

The term "tailed", in the context of a tailed primer, refers to a primer that has a region (e.g., a region of at least 12-50 nucleotides) at its 5' end that does not hybridize to the same target as the 3' end of the primer.

The term "dNTP mix" is intended to refer to mixture of deoxyribonucleotides that correspond to G, A, T and C that can be incorporated by a polymerase into a growing polynucleotide strand. A dNTP mix may contain dGTP, dATP, dTTP and d'''CTP (5-methyl dCTP and/or hydroxymethyl dCTP) as well as other deoxyribonucleotides, e.g., dCTP. In use, the dNTPs may each be at a working concentration of 50 µM to 1 mM (e.g., 100 µM to 500 µM, or 150 µM to 300 µM).

The term "treating" is intended to refer to contacting a product (e.g., DNA) with a reagent (e.g., an enzyme), under conditions suitable for the reagent to cause a change in (e.g., fragment) the product.

The term "methylation-dependent restriction endonuclease" is intended to refer to an enzyme that cleaves at or adjacent to a recognition site that contains a methylated cytosine. These enzymes cleave DNA if the cytosine in the site is methylated and do not cleave DNA if the cytosine is unmethylated. Methylation-dependent restriction endonucleases include, but are not limited to: MspJI family restriction endonucleases (described below), TypeIIM restriction endonucleases such as DpnI, GlaI, GluI, BisI, BlsI, and PcsI enzymes, and TypeIV enzymes such as McrBC. See, e.g., U.S. Pat. No. 8,507,239.

The term "MspJI family restriction endonuclease" is intended to refer to a methylation-dependent restriction endonuclease that cleaves at a site that is 10-20 bases (e.g., $N_{12}/N_{16}$) downstream from methylcytosine. This family of enzymes is described in Cohen-Karni (Proc. Natl. Acad. Sci. 2011 108: 11040-5), WO2010075375 and U.S. Pat. No. 8,507,239, which are incorporated by reference for disclosure for examples of enzymes, methods by which the enzymes can be identified and tested, reaction conditions and enzyme activities. Exemplary MspJI family restriction endonucleases include MspJI, SgrTI, FspEI, LpnPI, AspBHI, SgeI, LpnPI and RlaI, although others are known and can be used in the present method. Reference to an enzyme, e.g., a MspJI family member, either generically or by name, is intended to refer to a wild type restriction endonuclease as well as variants of those endonucleases that have an amino acid sequence that is at least 95% identical to the wild type restriction endonuclease and that cleaves in a methylation-dependent manner.

The term "adjacent to the methylcytosine nucleotides" is intended to refer to a site that is within 20 bases of a methylcytosine. This terminology is used because MspJI family restriction endonucleases cleave just downstream from their recognition sites, and the recognition site contains a methylcytosine.

The term "random sequence" is intended to refer to a sequence composed of N's, where N can be any nucleotide. For example, a four base overhang of random sequence has the sequence NNNN, where the Ns can independently be any nucleotide. Double-stranded adaptors that contain an overhang of a random sequence, collectively, have an overhang composed of Ns and the individual adaptors have different overhangs.

The term "variable sequence" is intended to refer to a collection of different sequences. For example, a four base overhang of variable sequence has the sequence can have at least 2, at least 5, at least 10, at least 20, at least 50, at least 100, at least 500 or at least 1,000 or more different overhangs.

The term "directly ligating" is intended to refer to a ligation in which one molecule is ligated onto another molecule without having to fill in or polish any of the ends prior to ligation. For example, two double stranded molecules that have complementary four base 4' overhangs can be directly ligated to each other. Two molecules that are "filled in" or "polished" using a DNA polymerase and/or exonuclease prior to ligation are not "directly" ligated to one another.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies or fluorescent base cleaving methods such as commercialized by Pacific Biosciences.

The term "microbial genome" refers to genetic material (DNA or RNA) that is microbial in origin (e.g., from a bacterium, virus or eukaryotic pathogen such as Plasmodium, Leishmania, or Trypanosome) that can be used as a template. A microbe may have, for example, a host-pathogen relationship with a mammal. In other cases, the microbial genome may be derived from the microbiome that is associated with the host. The term "microbial genome" is intended to include DNA genomes and RNA genomes (which can be readily reverse transcribed to DNA and then amplified by RT-PCR).

DETAILED DESCRIPTION OF EXEMPLARY EMBODIMENTS

Providing herein, among other things, is a method for preparing a nucleic acid for sequencing. In some embodiments, the method comprises: a) amplifying a nucleic acid template using a dNTP mix that contains 5-methyl dCTP, thereby generating product nucleic acid molecules that contain methylcytosines; b) digesting the product nucleic acid molecules with a methylation-dependent restriction endonuclease, e.g., an MspJI family restriction endonuclease, thereby cleaving the product nucleic acid molecules at sites that are adjacent to at least some of the methylcytosines and producing fragments of the product nucleic acid molecules; and c) ligating double-stranded adaptors onto the ends of the fragments to produce adaptor-ligated products. In some embodiments the method may additionally comprise: d) amplifying the fragments using primers that hybridize to the adaptors to produce amplification products. Kits are also provided.

Figure 1:
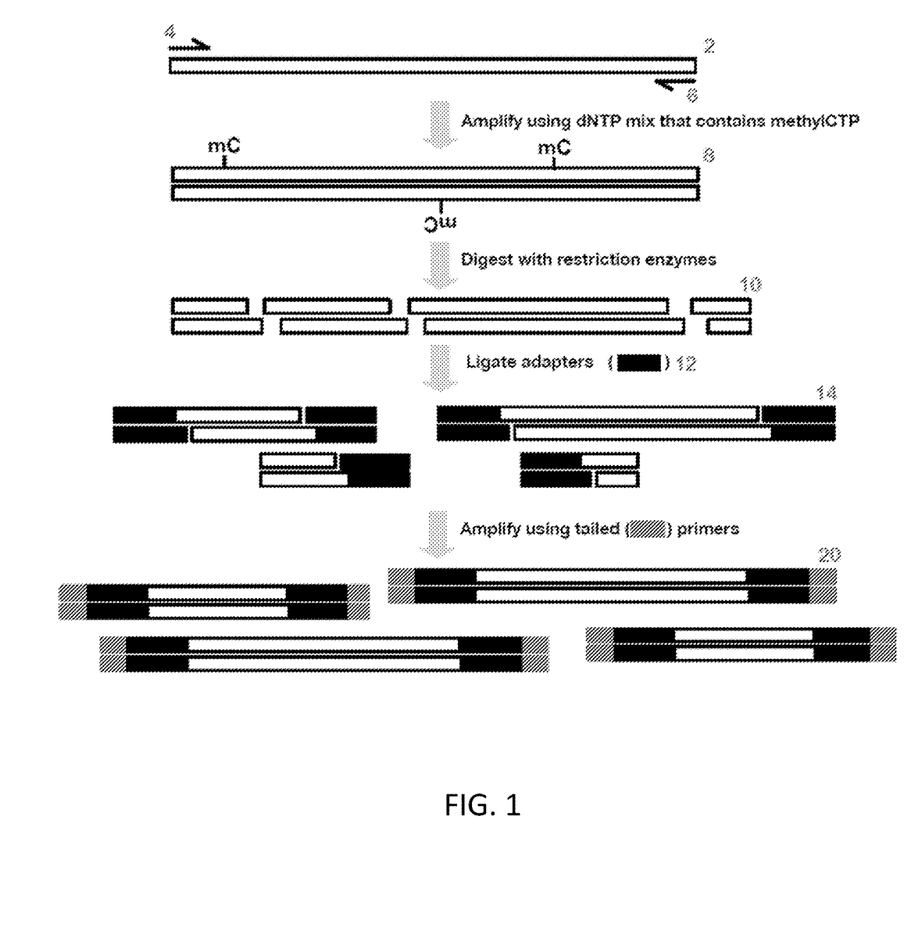
FIG. 1 schematically illustrates some of the general principles of the present method. As would be understood, except for the template molecules used at the beginning of the method, the nucleic acid molecules illustrated in this figure are double-stranded molecules.
Figure 2:
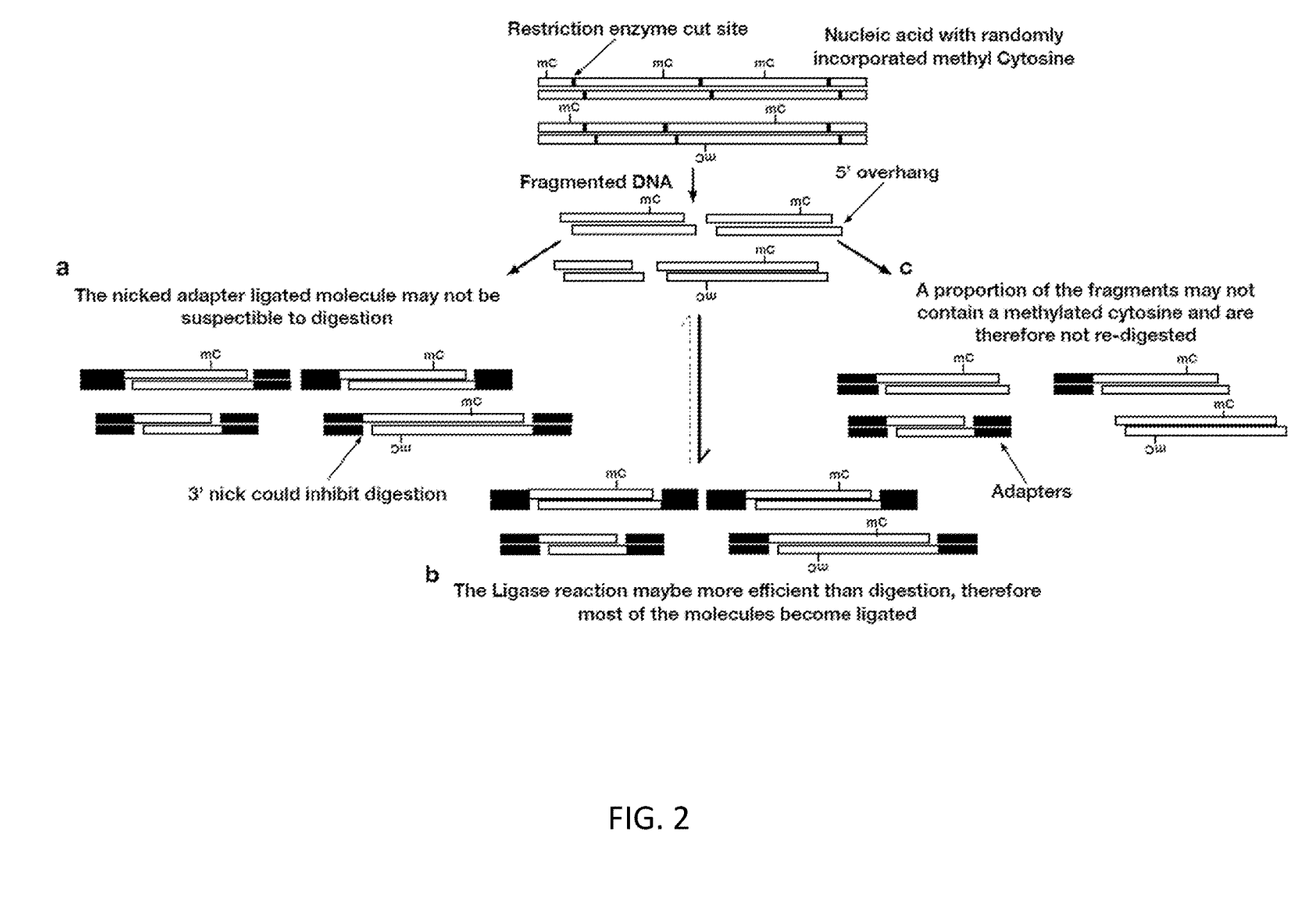
FIG. 2 schematically illustrates some of the potential reaction products that are produced when digestion and ligation are done in the same reaction.

Some of the general features of the present method are schematically illustrated in FIG. 1. With reference to FIG. 1, certain embodiments of the method may comprise: amplifying a nucleic acid template 2 using a dNTP mix that contains 5-methyl dCTP, thereby producing product nucleic acid molecules 8 that contain methylcytosines ($^m$C). This amplifying step may be done by isothermal amplification or by PCR, e.g., using primers 4 and 6. In some cases, the nucleotide mix may contain both 5-methyl dCTP and dCTP, in which case the molecules in product 8 will have both cytosines and methylcytosines, where the methylcytosines occupy different "C" positions in different molecules, as shown in FIG. 1. Only two product molecules are shown in FIG. 1. As would be recognized, product nucleic acid molecules 8 may be composed of at least $10^3$, e.g., at least $10^4$, at least $10^5$, at least $10^6$, at least $10^7$ or more molecules in which a portion of the C positions are methylcytosines. Each product molecule may contain, on average, at least 5, at least 10, at least 20, at least 50, at least 100, at least 500, or at least 1,000 or more methylcytosines (which may occupy at least 0.1%, at least 0.5%, at least 1%, at least 2%, at least 5%, at least 10%, at least 20%, at least 50% or at least 70%, up to 100% of total "C" positions). As will be described in greater detail below, one or more of primers 4 and 6, may contain one or more methylcytosines. The primers used may contain a mixture of methylated and unmethylated primers. In some cases, the amplification step may comprise circularizing the product and amplifying it using rolling circle amplification. In certain embodiments, the nucleotide mix may contain no dCTP. However, in many embodiments, the dNTP mix may contain both 5-methyl dCTP and dCTP, where the molar ratio the molar ratio of 5-methyl dCTP to dCTP in the nucleotide mix may be in the range of 1:1000 to 1000:1, e.g., 1:100 to 100:1 or 1:10 to 10:1. For example, the ratio the molar ratio of 5-methyl dCTP to dCTP in the nucleotide mix may be in the range of 1:1000 to 1:100, 1:100 to 1:10, 1:10 to 1:1, 1:1 to 1:10, 1:10 to 1:100 or 1:100 to 100:1000.

The product nucleic acid molecules 8 may be of any length depending on how the method is implemented. In some embodiments, the product nucleic acid molecules 8 may be 500 bp to 20 kb in length, although fragments that are at least 500 kb in length, e.g., 1 kb to 15 kb or 1 kb to 5 kb may be used in many cases. In some embodiments, if the product nucleic acid molecules 8 are made by rolling circle amplification, they may be up to 100 kb in length, or more. In certain cases (and depending on the molar ratio of 5-methyl dCTP to dCTP used, the method can be used to provide fragments of a defined size range (e.g., a median range in the size of, e.g., 200 bp to 500 bp or 250 bp to 750 bp, etc.) when used in conjunction with mammalian DNA, regardless of the concentration of that DNA in the sample.

In certain embodiments, the initial amplification reaction may be multiplexed so that the initial amplification reaction results in multiple (e.g., 2, 3, 4, 5, or 6 or more) different amplicons, where each amplicon is a different target sequence in the template.

The nucleic acid template 2 used in the method may be at any concentration and may be from any suitable source. In particular embodiments, the nucleic acid template may comprise genomic DNA from a eukaryote, e.g., human, monkey, rat, fish, insect or plant, etc., particularly a mammal, or from a microbe, e.g., virus or a bacterium. The concentration of the template may vary greatly and need not be known before starting the method. In some embodiments, there may be 1, 2, 3, 4, 5, up to 10, up to 100, up to 500, up to 1,000, up to 5,000, up to 10,000, up to 50,000 or up to 100,000 initial template molecules in the sample.

Methods for extracting DNA and RNA from various samples, e.g., clinical, forensic, and environmental samples, are well known in the art. Samples include, but are not limited to, skin swab, skin biopsy, saliva, tooth swab, tooth scrapping, cheek swabs, throat swab, sputum, endogastric sample, feces, urine, vaginal, cervical, endocervical, endometrial, nasal swab, lung, organ biopsy, and tissue biopsy. A sample can also be a bodily fluid. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit and urine. Methods for extracting total DNA from such samples are well known.

In particular cases, the template may be a DNA, an RNA virus or a reverse transcribing virus, e.g., reovirus, rotavirus, enterovirus, rhinovirus, hepatovirus, cardiovirus, aphthovirus, poliovirus, parechovirus, erbovirus, kobuvirus, teschovirus, coxsackie, norwalk virus, rubella virus, alphavirus, lymphocytic choriomeningitis virus, dengue virus, hepatitis C virus, yellow fever virus, influenzavirus A, influenzavirus B, influenzavirus C, isavirus, thogotovirus, measles virus, mumps virus, respiratory syncytial virus, Rinderpest virus, canine distemper virus, California encephalitis virus, hantavirus, rabies virus, Ebola virus, Marburg virus, corona virus, astrovirus, borna disease virus, arterivirus, equine arteritis virus, hepatitis E virus, retroviruses (e.g., HIV-1 and HIV-2) and hepatitis B virus.

The polymerase used in the initial amplification step may be any type of DNA polymerase. DNA polymerases can have 5' to 3' and/or 3' to 5' exonuclease activity. 'Proofreading' DNA polymerases are typically defined as those with 3' to 5' exonuclease activities. If this step is isothermal, then Bst 2.0, Bst LF, or phi29 DNA polymerase may be used. If the initial amplification is done by PCR, then a thermostable polymerase or bacterial or archael origin (or a variant thereof) should be used. Examples of non-proofreading thermostable polymerases (i.e., thermostable polymerases that do not have a 3' to 5' exonuclease activity) include, but are not limited to Taq and Tth. Examples of proofreading thermostable polymerases include, but are not limited to, Pfu (Agilent), Pwo (Roche), Tgo (Roche), VENT™ (NEB), DEEP VENT™ (NEB), KOD HiFi (Novagen), PFX50™ (Invitrogen), HERCULASE II™ (Agilent), PLATINUM PFX™ (Life Technologies) and ProofStart (Qiagen). These polymerases, on average, produce 4× to 8× fewer errors than Taq polymerase. Further examples of proofreading thermostable polymerases include, but are not limited to, PHUSION (NEB), PFUULTRA™ (Agilent), PFUULTRA™ II (Agilent), IPROOF™ (BioRad), and KAPAHIFI™ (Kapa Biosystems). These polymerases, on average, produce at least 20× fewer errors than Taq polymerase and can readily amplify fragments of up to 15 kb.

In certain embodiments, 5-methyl dCTP may be added to an RT-PCR reaction so that the reverse transcriptase incorporates methylcytosines into the first strand cDNA, and the DNA polymerase incorporate methylcytosines into the strands that are copied from the first strand cDNA.

After the product nucleic acid molecules 8 have been produced, they are treated with a methylation-dependent restriction endonuclease, e.g., a MspJI family restriction endonuclease, thereby cleaving the product nucleic acid molecules at sites that are adjacent to at least some of the methylcytosine and producing fragments 10 of the product nucleic acid molecules. This step can be done using MspJI, SgrTI, FspEI, LpnPI, AspBHI, and RlaI, or another suitable MspJI family restriction endonuclease. Reaction conditions for the use of these enzymes are known and, in certain cases, a relatively small portion of the amplification reaction may be used in the digestion.

As shown in FIG. 1, the restriction endonuclease cleaves the product nucleic acid molecules 8 at sites that are at or adjacent to the methylcytosines, thereby fragmenting the product nucleic acid molecules 8. Not all methycytosine-containing sites may be cleaved at this step because the enzyme used may have a sequence preference (for example, MspJI has a preference for mCNNG/A). As such, some fragments 10 may contain internal methylcytosines, but these do not interfere with future processing. Also, as mentioned above, the product nucleic acid molecules 8 may be digested (simultaneously or in series), by several different methylation-dependent restriction endonuclease, e.g., MspJI family restriction endonucleases, thereby producing smaller fragments as desired. Depending on the length of the product nucleic acid molecules 8 and the amount of 5-methyl dCTP used, the fragments produced may have an average size in the range of 150 bp to 1 kb, e.g., 300 bp to 700 bp, in length. This size range is preferable because it can be covered in a single sequencing read (either as a single read or using paired-end sequencing).

After fragments 10 have been produced, they are ligated to double-stranded adaptors, where the adaptors are ligated onto the ends of the fragments, to produce adaptor-ligated products 14. The double-stranded adaptors used in this step should have overhangs that are compatible with the ends of the fragments generated in the prior digestion. The sequences of the overhangs generated by digestion of the product 8 by the methylation-dependent enzyme depends on the sequence of the nucleic acid template and restriction enzyme used for digestion. Therefore, the sequences of the overhangs of the fragments can be predicted. As such, in some embodiments, the double-stranded adaptors used in this step may be specifically designed to have overhangs that are compatible with the predicted ends of the fragments. In some embodiments, the double-stranded adaptors may contain an overhang of variable or random sequence. So far, all MspJI family restriction endonucleases produce a four base 5' overhang and, as such, in some embodiments, the double stranded adaptors used in this step may be specifically designed to have four base 5' overhangs that are compatible with the predicted ends of the fragments. In these embodiments, the double-stranded adaptors may contain a 4 base overhang of variable sequence.

Because digestion with a MspJI family restriction endonuclease inherently results in product nucleic acid molecules that contain an overhang of a defined length, then the double-stranded adaptors also contains a 5' overhang of the same length. For example, if the MspJI family restriction endonuclease inherently results in four base 5' overhangs, then the double-stranded adaptors also contains a four base 5' overhang (which may be of variable sequence).

If other restriction endonucleases are used, then the adaptors can be redesigned as necessary. The adaptors provide binding sites for PCR primers that are used in the next step of the method and, as such, they usually are at least 12 bp long (e.g., at least 15 bp or at least 20 bp long). In certain cases, a Y adaptor, e.g., adaptor that contains: a double-stranded region and a single-stranded region in which the oligonucleotides are not complementary, may be used. In these cases, the end of the double-stranded region ligates to the fragments, and each strand of the product is asymmetrically tagged in that it has the sequence of one strand of the Y-adaptor at one end and the other strand of the Y-adaptor at the other end. In other embodiments, a loop adaptor (as described in U.S. Pat. No. 8,420,319 may be used).

In certain cases the adaptor may additionally contain a molecule identifier sequence, that assists in distinguishing the ligated molecules from one another after they have been amplified. In certain cases, the molecule identifier sequence may be error-correcting, meaning that even if there is an error (e.g., if the sequence of the molecular barcode is mis-synthesized, mis-read or is distorted by virtue of the various processing steps leading up to the determination of the molecular barcode sequence) then the code can still be interpreted correctly. Descriptions of exemplary error correcting sequences can be found throughout the literature (e.g., US20100323348 and US20090105959, which are both incorporated herein by reference). Such a molecule identifier sequence, and any other additional sequences, e.g., RNA polymerase promoters, sample identifiers, etc., should be positioned between the end that is ligated to the fragments and the primer binding sites. If a molecule identifier sequence is used, it can be of relatively low complexity (e.g., may be composed of a mixture of 8 to 1024 different sequences).

Alternatively, in some embodiments the molecule identifier sequence may be of high complexity, depending on the number of unique fragments that require identification.

In certain cases, the ligase and adaptors may be added directly to the digestion. In these embodiments, the a) restriction endonuclease is heat inactivated by, e.g., heating to a desired temperature for a period of time before b) adaptors and ligase are added to the reaction, and c) the reaction is at a temperature that is suitable for ligating the adaptors to the fragments.

In certain embodiments, the fragmentation and ligation steps can be combined into a single reaction, thereby reducing the time and number of steps required to generate adaptor-ligated fragments. In one embodiment, nucleic acid molecules are treated with methyl-sensitive restriction endonucleases and ligase in the same reaction. During the reaction, the restriction endonucleases cleave the nucleic acid molecules at sites that are adjacent to the methyl cytosine and these sites are then ligated to double-stranded adaptors. The ligated fragments could potentially be re-digested by the restriction enzymes as the reaction proceeds and result in no or very little ligated products. However, this is not the case and, at the end of the reaction, the majority of the products are ligated nucleic acid molecules containing the fragment of interest flanked by adaptors. This may be explained by one of the following three mechanisms: a) the nicked adaptor-ligated molecule is resistant to digestion; b) an equilibrium is established between the ligase and restriction endonucleases in which the ligation reaction is more efficient; c) following digestion, fragments that do not contain methylated recognition sites may be generated and these will be resistant to further digestion after ligation.

Because a restriction fragment must be ligated at both ends in order to be amplified and sequenced, the representation of fragments originating from the termini of the parental amplicon may sometimes be lower than the representation of those originating from the middle. In one embodiment, sequencing depth in the regions at the ends of the amplicons can be improved by incorporating one or more methylated cytosines (or other modified nucleic acids) into the RT-PCR primers. The methylated cytosines within the primers are placed in positions that generate recognition sites for a methylation sensitive restriction enzyme so that the amplicons generated have additional cut sites at each end and are therefore more likely to be ligated and sequenced. The methylated cytosines can be in 5' tails of the primers. The degree of increase in fragmentation at the ends of the amplicons can be adjusted by mixing the methylated primers with the equivalent un-methylated primers in varying ratios.

Finally and optionally, fragments 14 may be amplified using primers that hybridize to the adaptors, thereby producing amplification products 20. As shown in FIG. 1, the primers used to amplify fragments 14 have a 5' tail that provides compatibility with a particular sequencing platform. In certain embodiments, the method may further comprise sequencing amplification products 20. One or more of the primers used in this step may additionally contain a sample identifier. If the primers use a sample identifier, then products from different samples can be pooled prior to sequencing.

In some embodiments fragments 14 may be sequenced directly without being amplified. In these embodiments, either the adaptor (or a sequence that is added onto the adaptor by extending the fragment using an oligonucleotide as a template) may have a sequence that is compatible with use in a next generation sequencing platform as described below.

As would be apparent, the adaptors ligated to the fragments and/or the primers used for amplification may be compatible with use in a next generation sequencing platform, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. The present method may be used on any sequencing platform, including those that are based on sequencing-by-synthesis (i.e., by extending a primer that is hybridized to a template).

An implementation of the method is described below. This implementation uses a proofreading DNA polymerase such as Phusion, which does not incorporate dUTP but does incorporate 5-methyl-dCTP (2'-deoxy-5-methylcytidine 5'-triphosphate). In this implementation, the ratio of dCTP/d$^m$CTP can be used to control fragment length.

After PCR, the PCR products may be digested using a suitable restriction endonuclease, including FspEI, LpnPI, MspJI, and SgeI. All of these are methylation dependent type IIS restriction endonucleases of the MspJI family that have recognition sequences that include 5-methyl-cytosine and produce a four nucleotide 5' overhang of random sequence. For example, FspEI recognizes the 5 mC residue in the sequence C$^m$C and generates a four nucleotide 5' overhang by cutting the top strand 12 nucleotides downstream of the 5 mC, and cutting the bottom strand 16 nucleotides downstream of the 5 mC. In some cases the restriction enzyme can digest in PCR buffer. The fragmented DNA has the following features:

```
5- P- NNNN------------ -OH-3

3-OH- ------------NNNN -P -5
```

The overhang can then be ligated to an adaptor sequence with format:

```
                                                    (SEQ ID NO: 1)
5-OH- NNNNNXXXXXXXXXCTGTCTCTTATACACATCT -OH-3

(SEQ ID NO: 2)
3-OH-       XXXXXXXXGACAGAGAATATGTGTAGA -OH-5
``` where 5-XXXXXXXX-3 is a molecule identifier sequence and 5-AGATGTGTATAAGAGACAG-3 (SEQ ID NO:3) provides a primer binding site for later amplification. As an option (and as shown in this example), the adaptor does not have any 5' phosphates to prevent self-ligation. Theoretically, the ligation reaction can be performed in the same buffer as the digestion. The length of the molecule identifier sequence can vary depending on the application.

After digestion an excess of adaptors is ligated to fragmented DNA to produce a nicked product of the structure:

```
                                                          |nick
5OH-AGATGTGTATAAGAGACAGXXXXXXXXXGG-NNNN---NNNN  CCXX

XXXXXXCTGTCTCTTATACACATCT-OH3

3OH-TCTACACATATTCTCTGTCXXXXXXXXCC  NNNN---NNNN-GGXX
                                                nick|

XXXXXXGACAGAGAATATGTGTAGA-OH5
```

(top strand SEQ ID NO:4; bottom strand SEQ ID NO:5)

The ligated material is PCR amplified using primers that have 5' tails that provide compatibility with a next generation sequencing platform. In an exemplary method for use with the Illumina sequencing platform, the relevant primer sequences are as follows:

```
i5 primer (SEQ ID NO: 6):
5-AATGATACGGCGACCACCGAGATCTACAC[i5]TCGTCGGCAGCGT
CAGATGTGTATAAGAGACAG-3 i7 primer (SEQ ID NO: 7):
5-CAAGCAGAAGACGGCATACGAGAT[i7]GTCTCGTGGGCTCGGAGA
TGTGTATAAGAGACAG-3
``` where [i5] and [i7] are index sequences that distinguish different samples from one another, and the underlined sequences hybridize to the adaptors, and the 5' tails are compatible with Illumina's sequencing workflow.

In this example, the cycling profile has an initial incubation at 72° C. (without denaturation) to repair the nicks in the ligation products. In subsequent cycles, suppression PCR favours amplicons with i7/i5 rather than i7/i7 or i5/i5 Amplification yields a PCR amplicon that is compatible with typical workflow for Illumina's sequencing platform.

It is noted that the method described above may in certain instances be implemented using nucleotides other than 5-methyl dCTP. For example, several restriction endonucleases, particularly several methylation-dependent restriction endonucleases are also hydroxymethylation dependent in that they are capable of digesting DNA that contains methylcytosine or hydroxymethyl cytosine. As such, in certain cases, the method may be implemented as follows: a) amplifying a nucleic acid template using a dNTP mix that contains 5-methyl dCTP or 5-hydroxymethy dCTP (or a mixture thereof), thereby producing product nucleic acid molecules that contains methylcytosines and/or hydoxymethylcytosine; b) digesting the product nucleic acid molecules with a methylation-dependent or hydroxymethylation-dependent endonuclease (e.g., a MspJI family restriction endonuclease), thereby cleaving the product nucleic acid molecules at sites that are at or adjacent to at least some of the hydoxymethylcytosines and/or methylcytosines and producing fragments of the product nucleic acid molecules; c) ligating double-stranded adaptors onto the ends of the fragments to produce adaptor-ligated products; and d) amplifying the fragments using primers that hybridize to the adaptors to produce amplification products. Also provided is a comprising: a) a dNTP mix that contains 5-methyl dCTP; b) one or more hydroxymethyl-dependent restriction endonucleases (e.g., MspJI family restriction endonucleases); and c) double-stranded adaptors. The general principles described above can be applied to this alternative method and kit. Further, the method described above may be implanted using a single-stranded adaptors (i.e., adaptors that do not contain overhangs that are compatible with the fragments).

Kits

Also provided by this disclosure is a kit for practicing the subject method, as described above. A subject kit may contain at least: a) a dNTP stock that contains at least 5-methyl dCTP); b) one or more methylation-dependent (e.g., MspJI family) restriction endonucleases, as described above; and c) double-stranded adaptors (e.g., double-stranded adaptors that contain a 4 base 5' overhang of random sequence) as described above. The dNTP(s) in the stock may be in concentrated form (e.g., a 5× or 10× concentrate) relative to the working concentration described above and, as such, each dNTP may be at a concentration of 500 µM to 50 mM (e.g., 1 mM to 10 mM, or 1.5 mM to 5 mM). The double-stranded adaptors may comprise a four-base 5' overhang (which may be of variable sequence, as discussed above).

In addition, the kit may also comprise reagents for performing amplification (e.g., polymerase (e.g., a proof-reading polymerase), nucleotides and buffer, etc.), and other enzymes and/or reagents for performing the method, e.g., a restriction endonuclease, ligase, a primer, e.g., a primer that contains methylcytosine, etc. The various components of the kit may be present in separate containers or certain compatible components may be pre-combined into a single container, as desired. In certain cases, the dNTP stock contains both 5-methyl dCTP and dCTP. In these embodiments, the molar ratio of 5-methyl dCTP to dCTP in the nucleotide stock may be in the range of 0.01 to 99.9 or 99.9 to 0.01. For example, the molar ratio of 5-methyl dCTP to dCTP in the nucleotide mix may be in the range of 1:1000 to 1:100, 1:100 to 1:10, 1:10 to 1:1, 1:1 to 1:10, 1:10 to 1:100 or 1:100 to 100:1000. In some embodiments, the dNTP stock contains dGTP, dATP, dTTP, dCTP and 5-methyl dCTP, where the molar ratio of 5-methyl dCTP to dCTP in the nucleotide stock is described above.

In certain cases, the molar ratio of 5-methyl dCTP to dCTP in the nucleotide stock of the kit may be formulated to provide fragments of a particular size range (e.g., a median range in the size of, e.g., 200 bp to 500 bp or 250 bp to 750 bp, etc). when used in conjunction with mammalian DNA. In some cases, the vessel that houses the dNTP mix may be labeled with a size range of expected products.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc.

In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following example is provided in order to demonstrate and further illustrate certain embodiments and aspects of the present invention and are not to be construed as limiting the scope thereof.

Example 1

Template Amplification

Polymerase chain reactions were set up in 100 µL, volumes containing 1× Phusion HF buffer (NEB), 0.5 µM forward primer (5'-cagggccccctaggaaaaagg-3'; SEQ ID NO:8), 0.5 µM reverse primer (5'-ggctgacttcctggatgctt; SEQ ID NO:9), 0.02 units/µL Phusion Hot Start Flex DNA Polymerase (NEB) and 2 pg/µL of DNA template (HIV DNA clone supplied by the Aids Reagent Program). dNTPs were included at 200 µM for each of dATP, dGTP and dTTP. The combined concentration of dCTP and 5-methyl dCTP was 200 µM, and the percentage contribution of 5 methyl dCTP varied from 2% to 8% of the total amount of "dC" nucleotide in different reactions. For example, in the 2% reaction, the concentration of 5-methyl dCTP was 4 µM and the concentration of normal dCTP was 196 µM, giving a total concentration of 200 µM.

Figure 3:
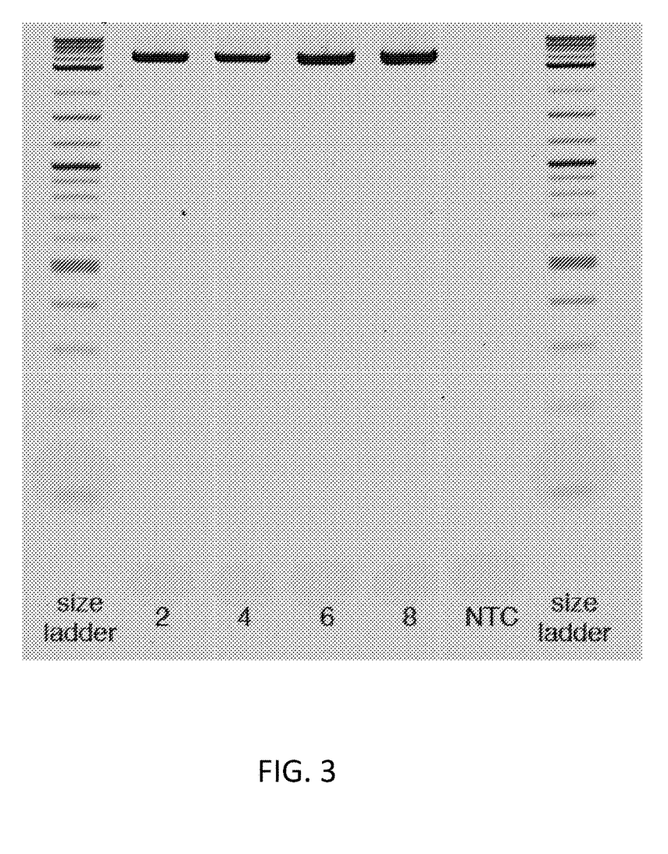
FIG. 3 is a gel showing PCR amplicons generated from reactions including varying amounts of 5-methyl dCTP. The numbers below each lane correspond to the percentage of 5-methyl dCTP used, so '2' means 2% 5-methyl dCTP with 98% dCTP. 'NTC' is the PCR no-template control. The size ladder is 2-log ladder from NEB.

The thermal cycling conditions were: 98° C. for 30 sec; 31 cycles of 98° C. for 10 sec, 64° C. for 30 sec and 72° C. for 2 mM; then 72° C. for 5 min followed by a hold at 4° C. 4 µL of each reaction was run on a 2% agarose gel to check amplification success (FIG. 3).

Example 2

Amplicon Fragmentation

The PCR amplicons generated from Example 1 were quantified on a Qubit fluorimeter. Each amplicon was then used in 11 different fragmentation reactions, each containing a different restriction enzyme or combination of restriction enzymes as below:

| Reaction number | Restriction enzyme(s) |
|---|---|
| 1 | FspEI |
| 2 | LpnPI |
| 3 | MspJI |
| 4 | SgeI |
| 5 | FspEI and LpnPi |
| 6 | FspEI and MspJI |
| 7 | FspEI and SgeI |
| 8 | LpnPI and MspJI |
| 9 | LpnPI and SgeI |
| 10 | No restriction enzyme (control) |

The volume of each digestion reaction was 18 µL, containing 1× modified digestion buffer (25 mM potassium acetate, 7.5 mM tris acetate, 9 mM magnesium acetate, 0.5 mM DTT), 0.1 mg/mL BSA, 1× enzyme activator (NEB), 0.167 U/µL restriction enzyme (total concentration) and 3.36 ng/µL of amplicon.

Figure 4:
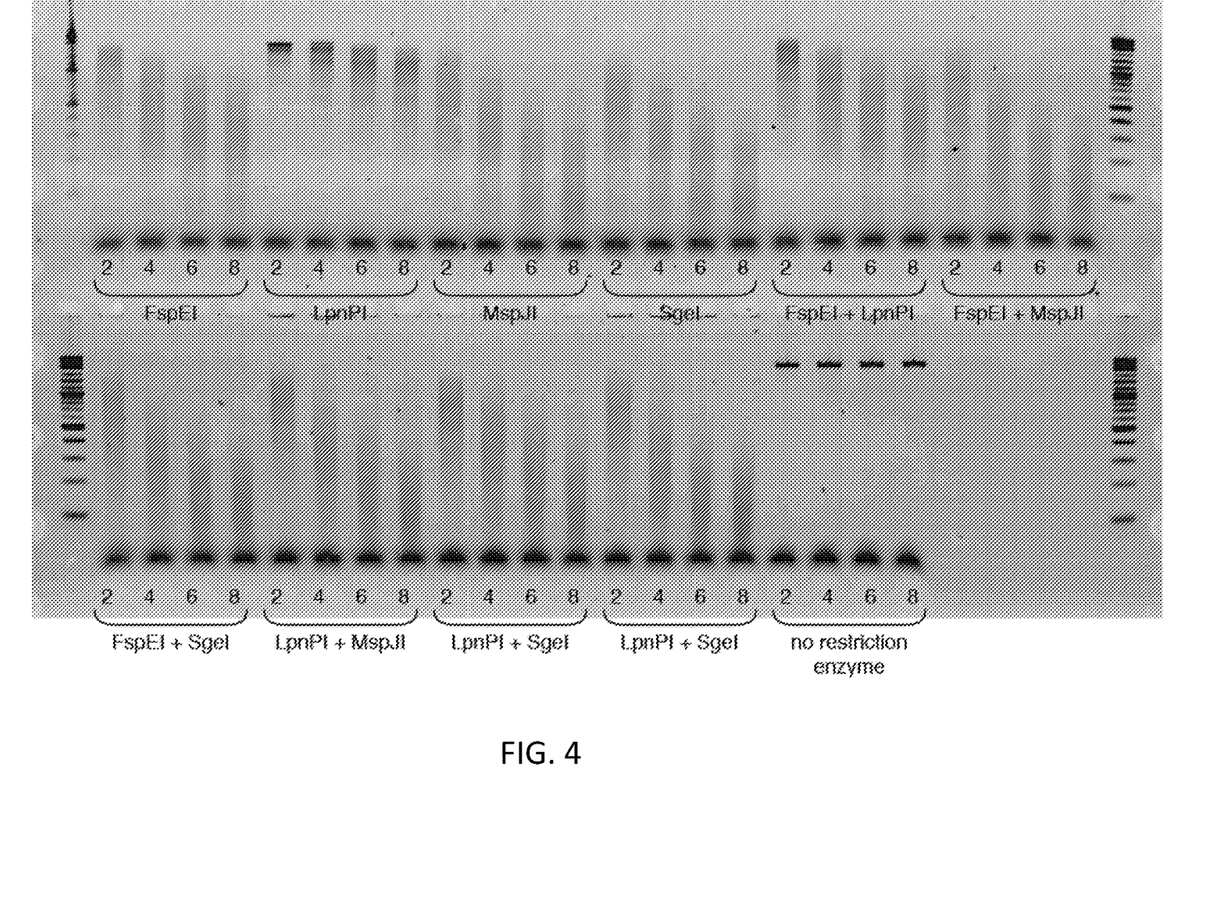
FIG. 4 is a gel showing the products generated by fragmenting the PCR amplicons from FIG. 2a with a range of restriction enzymes, both singly and in combination.

The amplicons were digested on a thermal cycler at 37° C. for 1 hour and the restriction enzymes were inactivated at 65° C. for 20 min then stored at 4° C. 3 µL of each was loaded onto a gel (FIG. 4) and the remaining 15 µL were used in the ligation reactions described below.

Example 3

Adaptor Ligation

To prepare the adaptors for ligation, the two strands of each were annealed together in 100 µL volumes containing 1× NEBuffer 4 (NEB) and 25 µM each adaptor strand. The mixes were heated to 95° C. for 5 min and then cooled down to 4° C. at a rate of −1° C. per minute. A total of 96 pairs of adaptors were annealed in this way, each containing a different 8-nucleotide molecule identifier sequence, sequence, shown as 'XXXXXXXX' in the schematic below:

After annealing, equal volumes of all 96 adaptors were pooled together to generate a 25 µM adaptor mix for use in the ligation reactions.

Ligations were set up in 30 µL reaction volumes containing 1× modified ligation buffer (38.75 mM Tris-HCl, pH 7.5; 9.5 mM DTT; 5 mM MgCl$_2$), 1 mM ATP, 5% PEG 8000, 0.42 µM annealed adaptors, 8 U/µL T4 DNA ligase (NEB) and 15 µL of digestion reaction products. Ligations were run on a thermal cycler at 16° C. before being stored at 4° C.

Example 4

Simultaneous Fragmentation and Ligation

The fragmentation and ligation steps can be combined into a single reaction, thereby reducing the time and number of steps required to generate adaptor-ligated fragments.

The combined fragmentation/ligation reaction was implemented using the following conditions: 10× NEB Buffer 4 1.5 µL, 100×BSA 0.15 µL, 30× Enzyme Activator (NEB) 0.5 µL, 5 µM annealed adaptors 0.25 µL, 100 mM ATP 0.15 µL, 0.2 U/µL MspJI (NEB) 0.25 µL, 0.2 U/µL FspEI (NEB) 0.25 µL, 2000 U/µL 0.25 µL, 0.2 ng/µL DNA from PCR and 3.95 µL nuclease free water. The reaction was incubated for 20 min at 37° C.

Example 5

PCR to Generate Sequencer-Ready Amplicons

Ligation products were purified using Agencourt AMPure XP beads (Beckman Coulter) according to manufacturer's instructions and eluted into 31 µL water.

The indexing primers used to amplify the ligation products were designed to be compatible with the Illumina MiSeq platform. Both the forward and reverse primers contained 8-base sample indexes, shown as NNNNNNNN below:

Forward indexing primer sequence:

Reverse indexing primer sequence:

(SEQ ID NO: 11)
5'-CAAGCAGAAGACGGCATACGAGATNNNNNNNNNGTCTCGTGG
GCTCGGAGATGTGTATAAGAGACAG-3'

Indexing PCRs were conducted in 50 µL reaction volumes, containing 1× Phusion HF buffer (NEB), 200 µM each dNTP, 200 nM forward indexing primer, 200 nM reverse indexing primer, 0.02 Phusion HS Flex DNA polymerase (NEB) and 30 µL of purified ligation product.

The thermal cycling conditions were: 72° C. for 3 min; 98° C. for 30 sec; then 25 cycles of 98° C. for 5 sec, 55° C. for 10 sec and 72° C. for 30 sec; then 72° C. for 1 min; then 4° C. hold.

Figure 5:
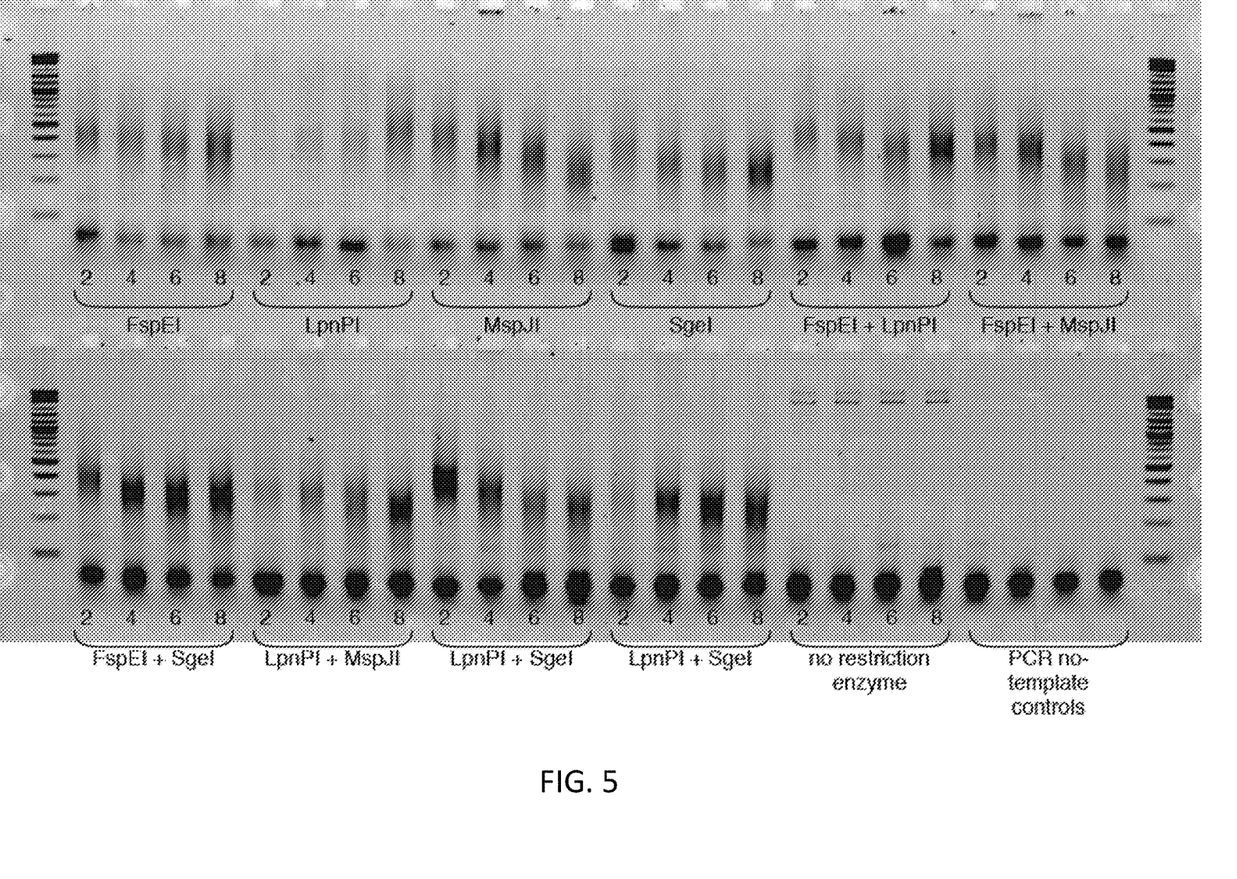
FIG. 5 is a gel showing indexing PCR products generated following adaptor ligation and amplification of the fragments from the gel in FIG. 4.

5 µL of each reaction was run on a 2% agarose gel (FIG. 5).

The invention claimed is:

1. A method for preparing a nucleic acid for sequencing, comprising:
   a) amplifying a nucleic acid template using a dNTP mix that contains 5-methyl dCTP, thereby producing product nucleic acid molecules that contain methylcytosines;
   b) digesting the product nucleic acid molecules with a MspJI family restriction endonuclease, thereby cleaving the product nucleic acid molecules at sites that are adjacent to at least some of the methylcytosines and producing fragments of the product nucleic acid molecules that contain four-base 5' overhangs; and
   c) directly ligating double-stranded adaptors onto the 5' overhangs of the fragments to produce adaptor-ligated products.

2. The method of claim 1, further comprising:
   d) amplifying the fragments using primers that hybridize to the adaptors to produce amplification products.

3. The method of claim 1, wherein the amplifying step a) is an isothermal amplification.

4. The method of claim 1, wherein the amplifying step a) is by PCR.

5. The method of claim 1, wherein the product nucleic acid molecules of a) are at least 500 bp in length.

6. The method of claim 1, wherein the nucleic acid template is a microbial genome.

7. The method of claim 6, wherein the microbial genome is a viral genome or a bacterial genome.

8. The method of claim 1, wherein the nucleic acid template is a mammalian genome.

9. The method of claim 1, wherein the amplifying step a) is done using a proof-reading polymerase.

10. The method of claim 1, wherein the dNTP mix contains both 5-methyl dCTP and dCTP.

11. The method of claim 10, wherein the molar ratio of 5-methyl dCTP to dCTP in the nucleotide mix is in the range of 0.01 to 99.9.

12. The method of claim 1, wherein the double-stranded adaptors of step c) comprise a four base 5' overhang of random sequence.

13. The method of claim 1, wherein the restriction endonuclease is selected from the group consisting of FspEI, LpnPI, MspJI, and SgeI.

14. The method of claim 1, wherein the digesting step b) comprises digesting the product nucleic acid molecules with a plurality of different MspJI family restriction endonucleases.

15. The method of claim 1, wherein the fragments produced in b) are in the range of 150 bp to 1 kb in length.

16. The method of claim 1, further comprising sequencing the adaptor-ligated products of c) or amplification products thereof.

17. The method of claim 1, wherein the digesting and ligating occur simultaneously in the same reaction.

18. The method of claim 1, wherein the amplification step a) is done using one or more primers that contain at least one methylcytosine.

19. A kit comprising:
   a) a dNTP mix that contains at least 5-methyl dCTP;
   b) one or more MspJI family restriction endonucleases; and
   c) double-stranded adaptors that comprise a four-base 5' overhang.

20. The kit of claim 19, wherein the dNTP mix contains both 5-methyl dCTP and dCTP.

21. The kit of claim 20, wherein the molar ratio of 5-methyl dCTP to dCTP in the nucleotide mix is in the range of 0.01 to 99.9.

22. The kit of claim 19, further comprising a polymerase and a ligase.

23. The kit of claim 19, wherein the polymerase is a proof-reading polymerase.

24. The kit of claim 19, wherein the one or more MspJI family restriction endonucleases are selected from the group consisting of FspEI, LpnPI, MspJI, and SgeI.

25. The kit of claim 19, wherein the double-stranded adaptors of c) comprise a four base 5' overhang of random sequence.

26. The kit of claim 19, further comprising a primer that comprises methylcytosine.

27. The method of claim 1, wherein the method is done in the absence of nick translation.

* * * * *